United States Patent
Kuo et al.

(10) Patent No.: US 6,210,954 B1
(45) Date of Patent: Apr. 3, 2001

(54) PROTEASE A-DEFICIENT *SACCHAROMYCES CEREVISIAE*

(75) Inventors: Tsong-teh Kuo; Dz-chi Chen, both of Taipei (TW)

(73) Assignee: National Science Council, Taipei (TW)

( * ) Notice: Subject to any disclaimer, the term of this patent is extended or adjusted under 35 U.S.C. 154(b) by 0 days.

(21) Appl. No.: 09/182,377

(22) Filed: Oct. 29, 1998

(51) Int. Cl.$^7$ ................ C12N 1/14; C12N 1/16; C12N 1/18; C12N 15/00; C12P 21/06
(52) U.S. Cl. ............... 435/254.2; 435/69.1; 435/200; 435/252.3; 435/255.2; 435/320.1
(58) Field of Search ................... 435/243, 252.3, 435/69.1, 200, 255.2, 320.1; 530/350, 403

(56) References Cited

PUBLICATIONS

Bitter et al., "Expression of heterologous genes in *Saccharomyces cerevisiae* from vectors untilizing the glyceraldehyde–3–phosphate dehydrogenase gene promoter", Gene 32:263–274 (1984).

Chen et al., "Abnormal growth induced by expression of HBsAg in the secretion pathway of *S. cerevisiae* pep4 mutants", Curr Genet 27:201–206 (1995).

Kim et al., "High–Efficiency, One–Step Starch Utilization by Transformed Saccharomyces Cells Which Secrete Both Yeast Glucoamylase and Mouse α–Amylase", Applied and Environmental Microbiology, Apr. 1988, p. 966–971.

Teichert et al., "Lysosomal (Vacuolar) Proteinases of Yeast Are Essential Catalysts for Protein Degradation, Differentiation, and Cell Survival", The Journal of Biological Chemistry, 264(27):16037–16045 (Sep. 25, 1989).

*Primary Examiner*—Ponnathapu Achutamurthy
*Assistant Examiner*—Manjunath N. Rao
(74) *Attorney, Agent, or Firm*—Fish & Richardson P.C.

(57) ABSTRACT

A stable protease A-deficient host strain of *Saccharomyces cerevisiae*, which undergoes a pseudohyphal-like growth mode when starved for a nitrogen source and is capable of expressing and secrets a heterologous protein when transformed with a secretion vector containing a DNA sequence which encodes the heterologous protein. Also disclosed is a *Saccharomyces cerevisiae* transformant obtained by transforming such a strain with a secretion vector containing a DNA sequence which encodes a desirable heterologous protein.

6 Claims, No Drawings

PROTEASE A-DEFICIENT SACCHAROMYCES CEREVISIAE

BACKGROUND OF THE INVENTION

Research efforts have been made to develop a recombinant yeast capable of expressing a heterologous protein, e.g., hepatitis B surface antigen (HBsAg), in the secretion pathway, thereby simplifying the purification of the yeast-derived recombinant protein.

The gene product of PEP4, protease A, regulates several yeast vacuolar hydrolases at the post-translational level. Woolford et al., Mol. Cell Biol. 6: 2500–2510, 1986. In earlier studies, HBsAg expressed in the secretion pathway was found to be toxic to various protease A-deficient strains of host yeast. See, e.g., Jones, Genetics 85: 23–33, 1977; Zubenco et al., Genetics 102: 679–690, 1982; and Achstetter et al., Yeast 1: 139–157, 1985. According to a more recent report, such toxicity could be progressively reduced in media containing lower concentrations of ammonium sulphate; the non-inhibitory transformants thus obtained were characterized by the phenotypes of enlarged cell and colony morphology, dimorphic transition to pseudohyphal-like and invasive growth in nitrogen-starved solid media, increase in HBsAg particle production, and enhancement of growth rate in liquid media. Chen et al., Curr Genet 27: 201–206, 1995.

SUMMARY OF THE INVENTION

The present invention features a stable protease A-deficient host strain of *Saccharomyces cerevisiae*, which undergoes a pseudohyphal-like growth mode when starved for a nitrogen source and is capable of expressing and secrets a heterologous protein (e.g., HBsAg or α-amylase) when transformed with a secretion vector containing a DNA sequence which encodes the heterologous protein. A strain is protease A deficiency if no or only residual activity can be detected by the APE test (described below).

This strain, preferably, is further characterized by one or more of the following parameters: a cell volume of 150 $\mu m^3$ at 28° C., a generation time of 90 min at 28° C., a viability rate of 45% at 37° C., a cell density of 7×10$^8$ cells/ml at 37° C., a cell mass of 14 OD$_{600}$ units at 37° C., a colony diameter of 2 mm at 28° C., a viability rate of 65% at 28° C., a cell density of 4.5×10$^8$ cells/ml at 28° C., a cell mass of 9.2° D$_{600}$ units at 28° C., and a higher growth rate at 37° C. than at 28° C. and a higher growth at 28° C. than at 20° C. All of such parameters can be measured employing the methods, materials, and conditions described in an actual working example provided below. Note that the above-recited values of the parameters are minima and a strain which exhibits one or more higher values is within the scope of this invention.

Also contemplated within the scope of this invention is a transformed *Saccharomyces cerevisiae* obtained by transforming the strain described above with a secretion vector containing a DNA sequence which encodes a desirable heterologous protein such as HBsAg or α-amylase.

The present invention also features a high-proliferative host strain of *Saccharomyces cerevisiae* obtained by a process which includes the following steps: (1) transforming cells of a protease A-deficient *Saccharomyces cerevisiae* parent strain, e.g., 20B12 (CCRC Accession No. 51837, Taiwan), with a secretion vector that expresses and secrets a heterologous protein which inhibits the growth of the transformed cells; (2) cultivating the transformed cells in a medium containing a reduced nitrogen source and selecting a non-inhibited mutant strain, the non-inhibited mutant strain having unstable phenotypes; (3) maintaining cells of the unstable non-inhibited mutant strain in the stationary phase for an extended period of time and selecting a stable non-inhibited mutant strain; and (4) growing cells of the stable non-inhibited mutant strain under conditions which favor the removal of the secretion vector to obtain a high-proliferative strain of *Saccharomyces cerevisiae*. NI-C (CCRC Accession No. 920007, Taiwan) is a high-proliferative strain obtained by the just-described method. A strain obtained by transforming such a high-proliferative strain with a secretion vector containing a DNA sequence which encodes a heterologous protein (e.g., HBsAg or α-amylase) is also within the scope of this invention. An example of transformants thus prepared is pYAS/12S-transformed NI-C (CCRC Accession No. 940112, Taiwan).

Other features or advantages of the present invention will be apparent from the following detailed description and also from the appending claims.

DETAILED DESCRIPTION OF THE INVENTION

Studies of the non-inhibitory (NI) yeast HBsAg-expressing transformants described by Chen et al. (see Id.) show that their NI phenotypes (defined as: enlarged cell and colony morphology, increase in HBsAg particle production, and enhancement of growth rate) are not stable and degenerate after several subcultures in non-selective broth. A long-term cultivation of NI transformants in the stationary phase has led to an unexpected discovery that the survival cells display more stable NI phenotypes than their parent NI transformants, i.e., having NI phenotypes that remain unchanged following repeated subculturing.

Culturing a stable NI transformant thus obtained under conditions which favor the curing of the secretion vector enables one to acquire a stable host strain, NI-C. NI-C cells are capable of receiving a secretion vector and expressing a desirable heterologous protein encoded by a DNA sequence in that vector. Also, they undergo pseudohyphal-like growth after a long-term (e.g., two weeks) cultivation under nitrogen-starved conditions. An appropriate reporter gene, such as mouse α-amylase, can be used as a positive selective marker for NI-C cells as this novel variant is able to proliferate on nitrogen-starved starch plates to form transformed colonies.

Without further elaboration, it is believed that one of ordinary skill in the art can, based on the above description, utilize the present invention to its fullest extent. The specific examples described below are, therefore, to be construed as merely illustrative, and not limitative of the remainder of the disclosure in any way whatsoever. Further, all publications cited herein are incorporated by reference.

EXAMPLES

Materials and methods

*Saccharomyces cerevisiae* 20B12 (Matα, trpl, pep4) is a protease A deficient strain (Jones, Genetics 85: 23–33, 1977). NI-20B12, a transformant of 20B12 which is not inhibited by the cytotoxic expression of cloned HBsAg of plasmid pYAS/12S, and construction/mapping of plasmid pYAS/12S and pYAS are described in Chen et al., Curr Genet 27: 201–206, 1995. pMA56 is a vector with ADH1 promoter (Valenzuela et al., Nature 298: 347–350, 1982). pMS12 is a vector derived from pMA56 with ADH1-promoter directed expression and secretion of mouse salivary α-amylase (Kim et al., Appl Eviron Microbiol 54: 966–971, 1985). pUC8/HBV is pUC8 with a full HBV DNA insert at the EcoR1 site. Plasmid pYE8 contains the glyceraldehyde-3-phosphate dehydrogenase (GAPDH) promotor (Holland et al., J Biol Chem 255: 2596–2605, 1980).

YPD complete medium contained 2% Bacto-peptone (Difco), 1% Bacto-yeast extract (Difco) and 2% dextrose (BDH). Transformants were grown in SD medium containing 0.17% yeast nitrogen base without amino acids (Difco), 0.5% ammonium sulfate (Serva) and 2% dextrose or in YNBD medium containing 0.17% yeast nitrogen base without amino acids and ammonium sulfate, 0.5% ammonium sulphate and 2% dextrose. Nitrogen-diluted starch medium (1/500 to 1/7000 YPS) was made of 1/500 to 1/7500 diluted YP (1% yeast extract and 2% peptone) and 2% soluble starch (Sigma). Yeast transformation was performed as described in Chen et al., Curr Genet 21: 83–84, 1992.

All the chemicals were analytical grade purchased from different resources (Boehringer Mannheim, BDH, Merck, Serva, or Sigma). Restriction enzymes were purchased from Boehringer Mannheim.

The protease A activity was detected by the APE test: Replica strains to thick YPD plate (40–45 ml/100-mm plate) and grown for 3 days at 30° C. To form the overlay mix, 2.5 ml of the ester solution (N-acetyl-DL-phenylalanine β-naphthyl ester: make a solution of 1 mg/ml dimethylformamide) was added to 4 ml of molten agar (0.6% agar, molten, held at 50° C.) in a 13×100 mm tube. The solution was vortexed until the schlieren pattern disappeared. After the bubbles exited, the contents was poured over the surface of colonies. After 10 min, the surface of the agar was carefully flooded with 4.5–5 ml of a solution of Fast Ganet GBC (prepared freshly, 5 mg/ml 0.1 M Tris-HCl, pH 7.3–7.5). The agar was allowed to stand for 5–10 min at room temperature, while watching the color development, the fluid was poured off when $CpY^{30}$ colonies turn red.

Southern analysis of genomic DNA was performed as follows: Yeast was cultured in YPD broth at 28° C. and harvested at late log phase. Genomic DNA was isolated from yeast cells according to the methods of Cryer et al. (Cryer et al., Methods Cell Biol 12: 39–44, 1975) Genomic DNA was treated with restriction enzyme EcoRI (45 U/μl) at 37° C. overnight as plasmid pYAS/12S was digested with EcoRI enzyme and produce 8.8 and 1.5 kb bands. 10 μg DNA was loaded in each well. Electrophoresis was performed on a 0.8% agarose gel. After being neutralized, Southern blot was performed as described by Bronstein et al. BioTechniques 8: 310–314, 1990. DNA was transferred onto nylon membranes and then cross-linked by UV light. Probes were prepared from dissected fragments of plasmid pYAS/12S, pUC8/HBV and pBR322 then labeled with Biotin-21-dUTP. After hybridization, chemiluminescent substrate solution was added to react with DNA. Finally the Southern blot was imaged on X-ray film for 1–4 hr and then developed.

Histone H1 kinase assay was modified from the protocol described in Moreno et al., Cell 58: 361–372, 1989). More specifically, samples containing $5 \times 10^7$ cells were spun down and washed twice at 4° C. with 3 ml ice-cold stop mix (0.9% NaCl, 1 mM NaN3, 10 mM EDTA, 50 mM NaF), and resuspended in 20 μl of ice-cold HB buffer (60 mM β-glycerophosphate, 15 mM p-nitrophenylphosphate, 25 mM MOPS [pH 7.2], 15 mM $MgCl_2$, 15 mM EGTA, 1 mM DTT, 0.1 mM sodium orthovanadate, 1 mM PMSF, 20 μg/ml leupeptin, 40 μg/ml aprotinin). About 1.5 ml of glass beads were added and the cells were broken by vortexing for 1 min. The beads were washed with 1 ml of HB buffer and the extract was centrifuged for 15 min at 100,000 rpm in a Beckman TL-100.2 rotor at 4° C. The protein concentration was adjusted to 1 mg/ml in each sample. For the kinase reactions, 4 μl of extract supernatant was pre-incubated with 6 μl of HB buffer containing 5 mM EGTA at 25° C. for 15 min. 10 μl of KIN buffer (1 mg/ml H1 histone [Boehringer Mannheim], 200 AM [γ-$^{32}$P]ATP, 100 cpm/pmol=40 μCi/ml in HB buffer containing 5 mM EGTA) were added and the reaction mixture were incubated for 20 min at 25° C. Reactions were terminated by the addition of 20 μl of 2×PAGE sample buffer, boiled for 3 min, and loaded on 11% SDS-PAGE minigels. Phosphorylated H1 histone was visualized by autoradiography after an overnight exposure at −70° C.

Mouse α-amylase activity was detected in two ways: comparison of clear-zone size on solid YPDS agar as previously described (Chen et al., J Biotechnol 29: 329–334, 1993), and quantification of secreted α-amylase activity in liquid YPD broth, culture supernatant was collected and buffered with 15 mM HEPES (pH 7.0) then assayed with an amylase detection kit (Sigma, procedure No. 577).

HBsAg particle assay was performed as follows: Cells at late log-phase (about $3 \times 10^7$ cells/ml) were harvested by centrifugation and resuspended in ice-cold lysis buffer (200 mM Tris, pH 7.4; 10 mM $MgCl_2$; 2 mM DTT; 1 mM EDTA; 0.5 μg/ml leupeptin; 0.7 μg/ml pepstatin; and 0.1 mM PMSF). Cells were broken in a violent vortex with 0.45-mm glass beads for 4 min at 4° C. HBsAg particles were detected by antibody against the spherical particle form of HBsAg with ELISA using an AUSZYME MONOCLONAL-ABBOTT kit.

Results

A detailed description of how to obtain NI-20B12 transformants of pYAS/12S from 20B12 is provided in Chen et al., Curr Genet 27: 201–206, 1995. Described below is a procedure of obtaining a stable and high-proliferative protease A-deficient host strain of this invention from the just-mentioned NI-20B12 transformants, which have been found to be unstable:

A 25-day long-term cultivation of unstable NI-20B12 transformants was performed to select survival transformants with more stable phenotypes. A transformant of 20B12 with plasmid pYAS was used as a control to compare the biological effect of expressed HBsAg on cell viability. Cells from each transformed colony were inoculated into SD broth at a density of about $10^6$ cells/ml, cultured at 28° C., 320 rpm, for 25 day. Samples of cells were taken throughout the time course and plated onto YPD plates at different densities ($10^2$–$10^6$ cells/plate) to calculate colony forming unit (CFU). The cell viability of each transformed cell sample was calculated as mean values from three independent ratios of CFU to the plated cell number on YPD plate. The cells of the pYAS control died rapidly while cells growing into the stationary phase with no CFU were detected after 206 hr cultivation. More specifically, the survival rate of the pYAS control group dropped to $10^{-6}$ on day 6, while pYAS/12S-NI still had a survival rate of $10^{-3}$ on day 6 and did not drop to $10^{-4}$ to $10^{-6}$ until day 25 (600 hours). The surviving colonies were picked and compared with the parent NI transformants.

It was found that the colony morphology was more stable than the parent NI strain. The surviving colonies grew in filamentous form under nitrogen source starved conditions. Several surviving colonies of the 20 to 25th day were selected and compared for their stability of phenotypes and HBsAg production. One surviving NI transformant that exhibited the highest HBsAg production and shortest doubling time was chosen for further plasmid curing.

The chosen NI transformant was continuously cultivated in non-selective YPD broth (inoculated at a density of $5 \times 10^4$ cells/ml). After 100 hr, cells were sampled and spread on YPD agar then replicated onto YNBD plates to check the restoration of auxotrophic trpl marker. One trpl revertant that had lost the HBsAg production and heritage of the phenotypes of its parent NI strain was selected and designated as NI-C.

To detect if there was any residue of pYAS/12S DNA in the NI-C cell, a Southern analysis was performed for genomic and plasmid DNA of NI-C. The following probes were prepared and used: Trpl (Xba1-Pst1 cut of pYAS/12S), $2\mu$-ori (Xba1-Pst1 cut of pYAS/12S), α-factor promoter-leader (EcoR1-Sal1 cut of pYAS/12S), HBV (EcoR1 cut of pUC8/HBV), and pBR (EcoR1 cut of pBR322), with molecular weights of 0.65, 1.3, 1.2 and 3.2, and 4.3 kb, respectively. HBV DNA (a cloned 2.3 kb fragment of preS1-preS2-SAg-X region) and pBR322 DNA of pYAS/12S could not be detected in genomic DNA digested EcoR1. However, the other sequences, i.e., Trpl gene, $2\mu$-ori, and α-factor-promoter-leader, were still detectable (major bands at 3.5 and 1.8 kb, different from the predicted 8.8 and 1.5 kb bands). Another southern analysis of extracted yeast plasmid DNA displayed a similar pattern (major bands also appeared at 3.5 and 1.8 kb). The results indicate that the NI-C variant still contained partial rearranged pYAS/12S DNA and had lost all the cloned HBV and pBR322 DNA.

The comparison of proliferative ability of NI-C and 20B12 (as control of pep4 genotype) and TL154 (as control of wild type genotype) is summarized in Table 1 below:

TABLE 1

| Characteristics | S. cerevisiae NI-C | S. cerevisiae 20B12 | S. cerevisiae TL154 |
|---|---|---|---|
| Genetic markers | Matα, trpl, pep4 | Matα, trpl, pep4 | Matα, trpl, leu2 |
| Cell size (volume, $\mu m^3$)[a] | 148.54 +/− 41.47 | 48.23 +/− 20.08 | 45.37 +/− 18.21 |
| Colony size (diameter, mm)[b] | 1.81 +/− 0.43 | 0.92 +/− 0.23 | 1.45 +/− 0.32 |
| Optimal temperature (YPD, ° C.) | 37 > 28 > 20 | 28 > 37 > 20 | 28 > 20 > 37 |
| Cell density (cells/ml) at 28/37° C.[c] | $4.52 \times 10^8$/ $7.21 \times 10^8$ | $3.17 \times 10^8$/ $1.21 \times 10^8$ | $5.40 \times 10^8$/ $<1 \times 10^5$ |
| Cell mass ($OD_{600}$) at 28/37° C.[c] | 9.21/14.20 | 3.02/2.08 | 8.44/<0.01 |
| Viability (%) at 28/37° C.[d] | 64.30/44.44 | 22.40/1.71 | 61.53/0.12 |
| Generation time (min)[e] | 89.5 | 139.1 | 111.9 |
| Pseudohyphal growth on 1/5000 YPD[f] | + | − | − |

[a]Cell size was estimated from 30 cells in early stationary phase in YPD broth, 28° C., 320 rpm.
[b]Colony size was estimated from plated colonies at a density of ~50 colonies/YPD agar plate, 28° C., 48 hr.
[c]Cell density and cell mass was determined in YPD broth, 320 rpm, 227 hours.
[d]Cell viability was determined at 151 hours.
[e]Generation time was estimated from $5 \times 10^5$ to $5 \times 10^7$ cells/ml at 28° C. in YPD broth, 320 rpm.
[f]Pseudohyphal growth was determined at 28° C. for 14 days.

As shown in Table 1, the colony size and cell volume of NI-C were approximately 2 to 3 fold larger than those of 20B12. The estimated generation time of NI-C cells was 89.5 min which was shorter than 139.1 min of 20B12. NI-C reached the log phase more quickly than 20B12, and with cell mass nearly ten times that of 20B12 in the stationary phase at 37° C. NI-C grew well in liquid YPD at 37° C. with a cell density of up to $10^9$ cells/ml and $OD_{600}$ of up to 15–20, while the TL154 strain was not able to survive and the 20B12 only grew slowly with a cell density of about $10^8$ cells/ml and $OD_{600}$ up to 2–3. The NI-C variant also exhibited higher survival ability. It had a higher viability rate than 20B12, i.e., greater than 40% in liquid YPD at 28° C. and 37° C. even after being cultured for more than 150 hours. Also, while the optimal temperature in terms of growth rate for both 20B12 and TL154 was 28°, optimal growth of NI-C was observed at 37° C. Finally, NI-C grew much faster under a nitrogen-starved condition (1/5000 YPD) than 20B12, and performed pseudohyphal-like growth after a long-term (two weeks) cultivation while 20B12 did not.

A Histone H1 kinase activity assay was performed to compare the mitotic ability of NI-C and 20B12 cells after a simple synchronization by a carbon source starvation. More specifically, cells of NI-C and 20B12 transferred from YPD broth at log-phase ($5 \times 10^6$/ml) were washed and sub-cultured in YP+0.02 % glucose medium (medium for carbon source starvation). Twenty four hours later, 2% glucose was supplemented to restart the cell cycle of yeast cells. Then, at the 0, 2.5, and 4th hours after the glucose was added, cells of NI-C and 20B12 were harvested for measuring histone H1 kinase activity. The histone H1 kinase activity of NI-C variant did not disappear after a 24 hour carbon source starvation. After addition of 2% glucose, stronger and quicker mitotic ability of NI-C was indicated at the 2.5 and 4th hour. In contrast, the histone H1 kinase activity of 20B12 did not appear until the 4th hour after glucose added.

A commonly used pMA56 plasmid was used to transform the NI-C variant and the transformants were selected on YNBD agar. The transformed colonies were clearly seen at the second day (48 hours). In contrast, the transformed colonies of control strains (20B12 and TL154) needed about 3 to 4 days to be seen. This improvement in shortening the colony forming time is attributable to the increase in mitotic ability and the shortened doubling time as discussed above. A pMS12 plasmid which directs the heterologous secretion of mouse α-amylase was used to analyze and estimate the productivity of secreted heterologous proteins in the NI-C variant. It was found that the productivity could only be detected in YPD rich medium, and was very low in solid or liquid YNBD selective medium.

The α-amylase activities of transformed NI-C and 20B12 host cells were compared both by the clear zone size on a YPDS (YPD+2% starch) plate and in YPD broth. The detection of α-amylase activity on solid YPDS agar was performed as follows: NI-C and 20B12 host cells were transformed with mouse α-amylase secretion plasmid pMS12 and control plasmid pMA56 and selected on YNBD solid medium. Two single transformed colonies were picked up with a toothpick and spotted on YPDS (YPD+2% starch) solid medium at 35° C. After 36 hours, the size of the clear zone formed by the digestion of starch by mouse amylase was observed. The detection of α-amylase activity in YPD broth was performed as follows: 20B12 and NI-C were transformed with plasmid pMS12 for the expression and secretion of heterologous mouse α-amylase. The transformed cells were cultivated in a selective YNBD medium for 3 days to saturation, then transferred into YPD broth at an initial cell density of $10^8$ cells/ml, broth was sampled from the 1st to 5th day (cell density $10^{8-10^9}$). After centrifugation, the supernatant was harvest and buffered to pH 7.0 and the secreted α-amylase activity was quantified and indicated as units/$10^{11}$ cells. The results show that the NI-C mutant had improved secretion of heterologous mouse α-amylase at both 35 and 28° C.

Since the NI-C was improved in cell proliferation and heterologous secretion of α-amylase, experiments were conducted to explore the possibility of using the α-amylase gene as a positive selection marker to select NI-C transformants on starch plates. To achieve this purpose, glucose in the media composition was replaced with starch. A preliminary experiment with YPS medium, i.e., YP (nitrogen source; 10 g yeast extract/l and 20 g peptone/l)+2% soluble starch, failed since too many pseudo-transformants (no clear zone) grew. We further diluted the composition of nitrogen source (YP) in several modified-YP(1/1–1/7500)+2% starch plates to decrease the contamination of the carbon source (from yeast extract or peptone) that could be utilized by yeast cells, while comparing the NI-C with its original strain, 20B12, and another wild-type strain, TL154. 0.1 μg plasmid DNA of pMA56 and pMS12 were used for each transformation. The transformed colonies were then counted at the 10th day after transformation. The positive transformed colonies could be further confirmed via the visible clear zone around colonies. The results are shown in Table 2 below:

TABLE 2

| Plasmid | pMS12 | | | | pMA56 | | | |
|---|---|---|---|---|---|---|---|---|
| Diluted YP + 2% starch | 1/1000 | 1/2500 | 1/5000 | 1/7500 | 1/1000 | 1/2500 | 1/5000 | 1/7500 |
| TL154 | 0 | 0 | 2 | 0 | 0 | 0 | 2 | 0 |
| 20B12 | 0 | 0 | 0 | 0 | 0 | 0 | 0 | 0 |
| NI-C | 150 | 230 | 115 | 88 | 20 | 30 | 8 | 12 |

As shown in Table 2, only the NI-C strain could utilize the expressed and secreted mouse α-amylase to degrade starch as a carbon source and to form transformed colonies on almost all of the nitrogen-source-diluted starch selection plates (agar plate with 1/500 to 1/7500 dilution of YP+2% starch). Other compositions of diluted YP (1/1 to 1/500 dilution)+2% starch was not suited for selection because too many pseudo-transformants grew and competed with the growth of the true transformants. Thus, the NI-C was shown to be able to use mouse α-amylase as a positive selection marker to form transformed colonies on nitrogen-starved plates that contained starch as the sole carbon source although the frequency of background of pseudo- and non-transformed colonies was still high (i.e., 20/150 to 12/88).

pYE8/12S, which contains the GAPDH promotor, was also used to transform the NI-C variant to express HBsAg. A yield of 2.6 mg/l ($OD_{600}$=6.6 or cell density=$1.1 \times 10^8$) or 393.9 μg/l/$OD_{600}$. It was reported that when two other protease A-deficient strains of S. cerevisiae, 20B12 and RH218, were transformed with a GAPDH promotor-containing plasmid to produce HBsAg, yields of 0.5 μg/l/$OD_{600}$ and 10 μg/l/$OD_{600}$ were obtained, respectively. Bitter et al., Gene 32: 263–274, 1984. Thus, in small volume the HBsAg yield of NI-C was unexpectedly much higher than that of 20B12 and RH218.

Other Embodiments

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A high-proliferative host strain of *Saccharomyces cerevisiae* obtained by a process comprising:

transforming cells of a protease A-deficient *Saccharomyces cerevisiae* parent strain with a secretion vector that expresses and secrets a heterologous protein which inhibits the growth of the transformed cells;

cultivating the transformed cells in a medium containing a reduced nitrogen source and selecting a non-inhibited mutant strain, said non-inhibited mutant strain having unstable phenotypes;

maintaining cells of the unstable non-inhibited mutant strain in the stationary phase for an extended period of time and selecting a stable non-inhibited mutant strain; and growing cells of the stable non-inhibited mutant strain under conditions which favor the curing of the secretion vector to obtain a high-proliferative strain of *Saccharomyces cerevisiae*.

2. The high-proliferative strain of claim 1, wherein said parent strain is 20B12 (CCRC 51837).

3. The high-proliferative strain of claim 2, wherein said high-proliferative strain is NI-C (CCRC 920007).

4. A transformed *Saccharomyces cerevisiae* strain obtained by transforming the high-proliferative strain of claim 1 with a secretion vector containing a DNA sequence which encodes a heterologous protein.

5. The transformed *Saccharomyces cerevisiae* strain of claim 4, wherein said heterologous protein is hepatitis B surface antigen or α-amylase.

6. The transformed *Saccharomyces cerevisiae* strain of claim 5, wherein said transformed *Saccharomyces cerevisiae* strain is pYAS/12S-transformed NI-C (CCRC 940112).

* * * * *